United States Patent [19]
Baumann et al.

[11] Patent Number: 5,417,678
[45] Date of Patent: May 23, 1995

[54] LOW PROFILE OSTOMY FILTER

[75] Inventors: Nicholas R. Baumann; John L. Roche, both of St. Paul; James M. Larson, Minneapolis; Paul E. Hansen, Lake Elmo, all of Minn.

[73] Assignee: Minnesota Mining and Manufacturing Company, St. Paul, Minn.

[21] Appl. No.: 276,028

[22] Filed: Jul. 15, 1994

[51] Int. Cl.$^6$ ............................................. A61F 5/44
[52] U.S. Cl. ............................................. 604/333
[58] Field of Search .................... 604/333; 55/385.4

[56] References Cited

U.S. PATENT DOCUMENTS

| | | | |
|---|---|---|---|
| 3,971,373 | 7/1976 | Braun | 128/146.2 |
| 4,100,238 | 7/1978 | Shinomura | 264/49 |
| 4,203,445 | 5/1980 | Jessup et al. | 128/283 |
| 4,247,498 | 1/1981 | Castro | 264/41 |
| 4,274,848 | 6/1981 | La Gro | 55/387 |
| 4,318,406 | 3/1982 | McLeod | 604/333 |
| 4,427,425 | 1/1984 | Briggs | 604/333 |
| 4,433,024 | 2/1984 | Eian | 428/198 |
| 4,539,256 | 9/1985 | Shipman | 428/315.5 |
| 4,609,584 | 9/1986 | Cutler et al. | 428/156 |
| 4,726,989 | 2/1988 | Mrozinski | 428/315.5 |
| 4,824,718 | 4/1989 | Hwang | 428/284 |
| 4,824,719 | 4/1989 | Creyf et al. | 428/285 |
| 4,868,032 | 9/1989 | Eian et al. | 428/198 |
| 4,902,553 | 2/1990 | Hwang et al. | 428/156 |
| 4,957,522 | 9/1990 | Brassell | 55/316 |
| 5,025,052 | 6/1991 | Crater et al. | 524/104 |
| 5,207,970 | 5/1993 | Joseph et al. | 264/518 |
| 5,250,042 | 10/1993 | Torgalkar et al. | 604/333 |
| 5,260,360 | 11/1993 | Mrozinski et al. | 524/95 |

FOREIGN PATENT DOCUMENTS

0358316B1 10/1993 European Pat. Off. .

OTHER PUBLICATIONS

Report No. 4364, Naval Research Laboratories, May 25, 1954, "Manufacture of Superfine Organic Fibers" by Wente, V. A., Boone, C. D., and Fiuharty, E. L.

Primary Examiner—Jerome L. Kruter
Attorney, Agent, or Firm—Gary L. Griswold; Walter N. Kirn; William J. Bond

[57] ABSTRACT

A low profile heat-sealable adsorbent filter for ostomy appliances is provided. The filter comprises a heat-sealable microporous film layer, a filter layer of melt-blown microfibers loaded with adsorbent particles and a cover layer. The microporous film layer provides for rapid release of flatus or other gas in having a Gurley value of less than about 100 seconds/50 cc. The melt-blown microfiber filter web has an estimated service life of about 3 days or more with a web basis weight of about 700 grams/m$^2$ or less. The low profile filter can be sealed to the outside face of an ostomy appliance with a perimeter seal to provide a filter with no liquid or gas by-pass and no liquid by-pass through the filter.

20 Claims, 1 Drawing Sheet

LOW PROFILE OSTOMY FILTER

BACKGROUND AND FIELD OF THE INVENTION

This invention relates to a low profile filter for use in ostomy and related appliances such as ostomy and ileostomy pouches.

Ileostomy and ostomy pouches or appliances have long been fitted with adsorbent filters designed to filter malodorous gases discharged into the pouch or formed in the pouch. These filters are generally based on use of adsorbent particles such as activated carbon incorporated into a matrix such as polyurethane foam or a fibrous web. Liquid by-pass through the filter or around the filter or gas by-pass around the filter device have been the areas of major concern. In order to prevent these events from occurring, the adsorbent filter is frequently protected by a liquid impermeable and gas permeable barrier layer or film with the barrier film heat-sealed along a peripheral edge to the ileostomy or ostomy pouch or like device to prevent liquid bypass. A specific design addressing the problem of liquid and gas by-pass is described in U.S. Pat. No. 4,274,848, which proposes the use of a porous filter pad protected on at least one face by a heat-sealable protective layer which is porous and resists soiling and particle contamination. In a preferred arrangement the heat sealable layer would be formed of a cellulosic material treated to be heat-sealable (KAYCEL) optionally with an additional porous thermoplastic film layer such as DELNET or GORTEX. When the porous filter pad is exposed to a liquid environment it is preferred that the outermost film of the protective layer facing the liquid be a thermoplastic film such as GORTEX. Liquid bypass is prevented by providing a flexible liquid barrier film (23) which is separately and continuously heat-sealed to the two protective layers covering both faces of the porous filter pad, which isolates the filter from the liquid. This barrier film is then further heat-sealed to the plastic film forming the ileostomy or ostomy pouch, preventing liquid by-pass around the filter. The filter itself is located on the inside face of the ostomy pouch. The porous filter pads are described as preferably a fibrous web of thermoplastic fibers mixed with carbon in a 50/50 blend. This appliance is extremely complicated to manufacture requiring numerous assembly steps and heat-sealing operations, additionally the filter itself is quite bulky and even placed on the inside face of the appliance can create an unsightly bulge on the wearer.

Other internally placed filters in ostomy appliances are described in U.S. Pat. No. 4,203,445, U.S. Pat. No. 5,250,042, and European Patent No. 358 316 B1. In U.S. Pat. No. 4,203,445 a filter is described which is similar to that described in U.S. Pat. No. 4,274,848, however, without the flexible liquid barrier layer(the two protective layers extend beyond the filter and tho two layers are heat sealed to the pouch wall) and the outward facing filter protective layer is provided with a series of holes to increase gas flow. Gas by-pass of this filter is possible. U.S. Pat. No. 5,250,042 protects its filter with a multi-layer film barrier which is heat-sealed to the ostomy pouch around the filter. Suitable barriers described are laminates of a thermoplastic film and a porous polytetrafluoroethylene film, both of which are described as gas permeable. The actual filter is not protected and comprises carbon impregnated polyurethane foam with two nonwoven cover layers adhered on both sides. This again, is a rather high profile filter and it requires complicated assembly and manufacturing steps in order to produce the finished appliance. European Patent No. 358 316 B1 describes a polyurethane foam impregnated with carbon which is housed in a rigid thermoplastic filter case. The filter case is in turn heat-sealed to the inside wall of the ostomy appliance. This is an extremely high profile heavy filter and would be somewhat costly and uncomfortable for the wearer.

U.S. Pat. No. 4,957,522 describes a conventional filter surrounded by a liquid impermeable gas permeable film. The filter is described as usable in container vents such as for radioactive material or an ostomy appliance. Either the two outer faces or the outer faces and the side portions of the filter are covered with the microporous or porous film. No specific filter or microporous film is specified.

BRIEF SUMMARY OF THE INVENTION

An ostomy or like bag is provided comprising heat sealable(including conventional heat sealing and ultrasonic sealing) side walls, at least one side wall having an opening. On an outside face of the side wall opening a heat sealable ostomy bag filter is heat sealed to the side wall by a heat sealable microporous film layer of the invention filter. The invention filter comprises at least one outer heat sealable liquid impermeable, gas permeable microporous film layer having a Gurley number of less than about 100 seconds/50 cc, an inner filter layer of adsorbent particles uniformly dispersed in a melt-blown microfiber web having a particle loading level such that a 40 mm diameter filter would provide an estimated service life of greater than 3 days on a typical ostomy appliance and a second outer porous cover layer. The at least one outer heat sealable microporous film layer is on a first face of the inner filter layer and the porous cover layer is on a second face of the filter layer and the three layers are coextensive and continuous over the filter layer. The filter is sealed to the ostomy bag at a continuous outer periphery region of the filter which outer periphery includes the filter layer around the full periphery circumference. The filter layer is thin enough to allow the microporous film layer to be readily heat sealed to the ostomy bag through the filter layer. The filter is thin and conformable without liquid by-pass or gas by-pass around the filter.

DESCRIPTION OF THE PREFERRED EMBODIMENTS

Figure 1:
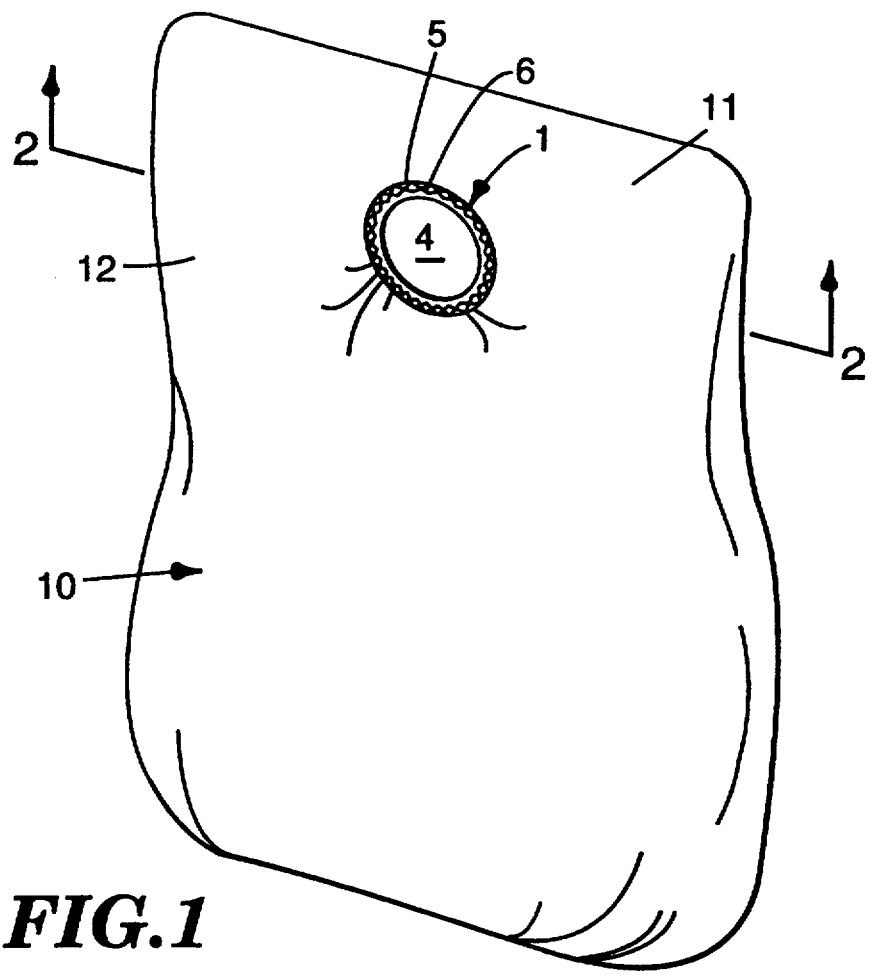
FIG. 1 is a top plane view of the invention ostomy filter attached to the outside face of an ostomy appliance.
Figure 2:
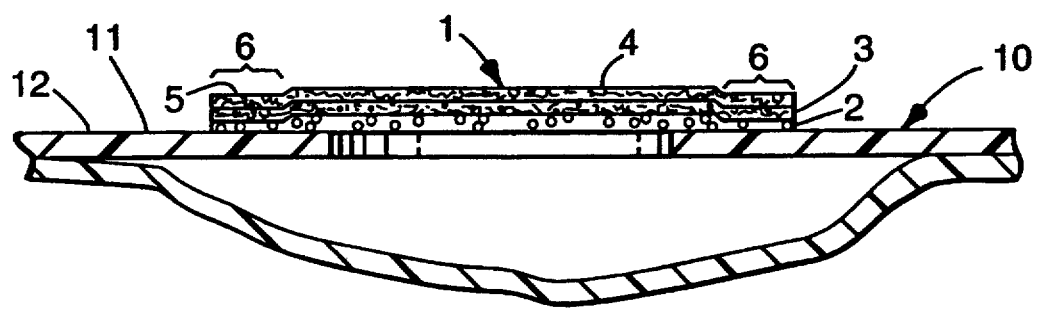
FIG. 2 is a cutaway side view of the invention ostomy filter attached to the outside face of an ostomy appliance.

Referring to FIG. 2 this is a side view of the invention filter 1 formed of a heat sealable microporous film layers 2, an adsorbent particle filled melt-blown microfiber web 3 filter layer and a porous cover layer 4. As shown in FIGS. 1 and 2 the filter 1 is heat sealed to the outer face of an ostomy bag 10 wall 11 along an outer periphery of the filter 1 by the microporous film layer 2. The three layers (2, 3 and 4) are coextensive and continuous over the filter layer. The coextensive and continuous layers (2, 3 and 4) extend into the heat sealed outer periphery 6 of the filter 1.

The microporous film layer must be heat sealable to the ostomy appliance 10 walls 11 which are conventionally a liquid and gas impermeable thermoplastic film or film laminate. The walls 11 are conventionally polymer or copolymer films which have one or more layers, such as one or two outer polyethylene or polyethylene vinyl acetate layer(s)coextruded with a polyvinylidene chloride inner layer. The microporous film would also be formed of a thermoplastic polymer, heat sealable to the outer face 12 of walls 11.

The filter 1 is heat sealed to an ostomy appliance wall 11 along the filter perimeter 5 by the heat sealable microporous film layer. This perimeter seal 6 is fluid tight. Consequently there is no portion of the filter 1 or filter seal 6 potentially open to fluid by-pass.

The heat sealable microporous film can be formed from a thermoplastic polymer which is provided with a series of interconnected pores with an effective pore size of 20 microns or less and most preferably 1 micron or less. The pores can be produced by any known method including mechanical working of a film, blending in solid particulates(the particles can range in diameter from 0.1 to 250 micrometers and be incorporated at levels ranging from 40 to 70 percent of the film) into the thermoplastic polymer forming the film and then orienting the formed film to create pores or use of a phase separating liquid or solid additive, which additives can be subsequently removed to by solvent extraction and which films can be oriented to increase porosity. Use of phase separable liquid additives are discussed in U.S. Pat. Nos. 4,902,553, 4,539,256, 4,609,584, 4,726,989 or 4,824,719. The material described in these patents comprises a microporous film formed by dissolving a crystallizable polymeric material in liquid additive at a temperature above the melt temperature of the polymeric material and forming this melt into a film, such as by extrusion. The homogeneous solution is then permitted to cool at a rate suitable to cause the crystallizable polymer to crystallize into a distinct interconnected phase, the polymer being incompatible with the additive at ambient or use conditions. The phase-distinct film material is then uniaxially or multiaxially orientated, creating a film with micropores, which pores contain the now phase-distinct liquid additive.

The additive liquid can be used in amounts ranging from about 5 to 80 percent by weight of the formed film, preferably 5 to 50 percent, and most preferably 10 to 30 percent. Nucleating agents such as those described in U.S. Pat. No. 4,824,718 and U.S. Pat. No. 4,726,989 can also be used to produce uniform crystallization of the polymeric material upon cooling.

Following precipitation of the thermoplastic crystallizable polymer, the film can be used unoriented or preferably orientated with a stretch ratio, in at least one direction, of 0 to 3, preferably from 1.5 to 2.5.

Discussions of crystallizable polymers and phase-separating additives are also found in U.S. Pat. No. 4,247,498 and U.S. Pat. No. 4,100,238. For example, for isotactic polypropylene, these patents describe, the use of phase-separable additives such as poly-1-butene, polyethylene wax, low molecular weight polyethylene, alcohols, aldehydes, amines, esters such as methylene benzoate, ethers such as diphenylether, hydrocarbons such as trans-stilbene or ketones.

Generally, the thickness of the microporous film is from 5 to 250 microns, preferably from 30 to 200 microns. Comparatively thinner films are preferred in terms of cost and increased moisture vapor permeability. However, too thin a film may be inadequate in providing an adequate level of strength to prevent the film from tearing in manufacturing or ordinary usage.

In a preferred embodiment, the heat sealable microporous film has a melt additive in the thermoplastic polymer to inhibit soil and particulate contamination of the film by ostomy solids. Such additives include fluorochemical and silicone polymer melt additives which dissolve or disperse in the thermoplastic polymer melt phase and are not destroyed by extrusion processing conditions. The additive must also be added in relatively low levels such as to not adversely affect the functional level of heat sealability of the thermoplastic microporous film to the ostomy appliance wall outer face. A suitable class of melt additives are described in U.S. Pat. No. 5,025,052 (fluoroaliphatic radical-containing oxazolidinone compounds), which additives can be added in amounts of up to 5 weight percent, preferably less than 2 weight percent so as to provide between 100 and 10,000 ppm fluorine to the film by weight.

The low profile filter layer 3 is a adsorbent particle loaded non-woven melt-blown microfiber web. The filter layer is formed by incorporating adsorbent particles into a melt blown web as the web is being formed as described, for example in U.S. Pat. Nos. 4,433,024, 4,868,032, or 3,971,373, the disclosures of which are incorporated herein by reference. The melt-blown microfibers are preferably formed of a thermoplastic polymer heat sealable to the microporous film layer 2. For example, if the microporous film is formed from polyethylene or polypropylene the melt-blown microfibers would preferably be formed from a polyolefin polymer such as a polyethylene polymer or copolymer heat sealable to the microporous film polyethylene. It is also possible to use multiple sources of different microfibers or multilayered microfibers, such as disclosed in U.S. Pat. No. 5,207,970 (Joseph et al.), when forming the web. Other components can be added as needed such as staple fibers or binding fibers, however, preferably the melt-blown microfibers are used alone in conjunction with the adsorbent particles to provide the lowest profile filter web.

The adsorbent particles are loaded into the melt-blown web at levels sufficient to provide a filter with at least a three day effective useful life (as described below). This can be a filter web with an activated carbon loading level of at least 0.25 grams, preferably at least 0.30 grams, with a 50 gm/m$^2$ carrier web having a diameter of 40 mm the web this loading level corresponds to a filter web with greater than 80 percent activated carbon particles, preferably greater than 85 percent activated carbon particles, by weight. However carbon loading levels of 0.15 grams are functional with more active carbons, with filter web carbon loading levels preferably greater than 60 percent. Generally this high loading level is preferred for all filter webs assuring high adsorption efficiency. The adsorbent particles are preferably activated carbon granules which have been treated to improve adsorption of acid gas. A suitable treatment would be to treat the activated carbon with $K_2CO_3$ or NaOH or like basic solution. Additionally a oxidative compound such as a KI can be used to treat the carbon, e.g. from an aqueous solution. The adsorbent particle loaded melt-blown microfiber filter web preferably has a thickness of less than about 5 millimeters, preferably less than about 2.5 millimeters, or a basis weight of less than 700 grams/m², preferably less than 500 grams/m² with the carrier web having a basis weight of less than less than 100 grams/m², preferably less than 60 grams/m².

The protective cover web 4 prevents loss of adsorbent particles and preferably is sufficiently dense to prevent passage of the adsorbent particles but preferably is more porous to the passage of air than the microporous film. Suitable porous cover webs include woven and non-woven fabrics such as melt-blown webs, consolidated spun bond fabrics, carded webs, and the like. Like the fibers of the melt-blown web forming the filter layer the fibers of the cover web are preferably heat sealable to the microporous film and/or to the filter layer melt-blown web fibers.

The multilayer filters can also be provided with other layers as required, all of which would preferably be heat sealable to each other. For example, a second microporous film could be used with, or instead of, cover web 4 when the filter is likely to be subject to external contamination.

The invention composite multilayer filter 1 is easily manufactured from the component webs and/or films, which are joined by ultrasonic welding, heat welding, adhesive bonding or mechanical engagement such as needling (provided that the microporous film is not needled). The component layers can be joined before, during or after they are formed into discrete filter elements. In a preferred embodiment the filters are die cut with heated die cut elements that also join the multiple layers together at the perimeter. The formed filters are also easily attached to an ostomy or ileostomy appliance by a single step peripheral heat bonding of the filter to the appliance outer wall around a hole(s) or slit. This provides a convenient, low cost, low profile filtered appliance without the manufacturing and performance problems of a filter which must be attached to an inside face of the appliance wall.

TEST PROCEDURES

Gas Deodorization Capacity

The test apparatus consisted of a test housing having the challenge gas supply source, a pressure gauge and a flowmeter on the upstream side of the housing and a $H_2S$ detector downstream of the housing. The test challenge gas consisted of an 80/20 (vol %) mixture of nitrogen and methane containing 25 ppm $H_2S$ which is passed through a 40 mm diameter filter test sample at a flow rate of 500 ml/min at ambient temperature. Filter samples are conditioned at $22+/-2°$ C. for 4 hours prior to testing. The end point of the filter effectiveness is defined as that point when the $H_2S$ concentration passing through the filter reaches a level of 2 ppm. The adsorption rate and capacity of the filter must be such that no more than 2 ppm $H_2S$ can be detected downstream of the filter for a period of at least 15 minutes, preferably at least 18 minutes. These criteria correspond to a design service life of at least 3 days under ordinary usage.

A design with a minimum life of 3 days was based on a maximum flatus handling capacity of about 7.5 liters (based on measurements demonstrating that the highest observed flatus passage in patients maintained on a typical western diet is about 2.4 liters/day). With the test challenge, 9 liters of flatus deodorized in 18 minutes correlates to 3.75 days of ordinary maximum challenge in typical use.

Permeability

A 40 mm diameter circular filter test sample is clamped in a test apparatus similar to that described above, except that it also has a flow meter downstream of the test housing, such that the perimeter of the test sample is secure and air tight. Differential air pressures of 2, 4, 6, 8, and 10 cm of $H_2O$ are then applied across the filter and the resultant air volume flow through the test filter determined. A minimum volume flow of 500 ml/min. at 10 cm $H_2O$ differential air pressure is required to pass the test.

Porosity

Porosity of the microporous film is measured according to ASTM-D-726-58 Method A and is reported in Gurley seconds/50 cubic centimeters (cc). Based solely on functional considerations, a Gurley Number of 1800 seconds/50 cc would provide a permeability level adequate to vent a flatus volume of 2.4 liter/day. However, patient comfort considerations require a more porous barrier material that will allow the ostomy bag to deflate rapidly (i.e. to vent approximately 500 cc of flatus in about 10 minutes). To meet this requirement the microporous film should have a Gurley number of less than about 55 seconds/50 cc, and more preferably a Gurley number of 42 sec/50cc, which would allow 500 cc of flatus to be vented in approximately 7 minutes. However, Gurley numbers of up to 100 seconds/50 cc would be acceptable for some applications.

EXAMPLES

Microporous Film Preparation

Microporous film compositions useful in the filter constructions of the present invention were prepared according to the procedures described in U.S. Pat. No. 5,260,360 (Morzinski et al.), which is incorporated herein by reference. Microporous films of the compositions indicated in Table I were prepared using a thermally induced phase separation technique by melt extruding the composition with a twin screw extruder operating at a decreasing temperature profile through a slip gap sheeting die onto a smooth steel casting wheel. The phase separated film was continuously oriented or stretched in the machine direction (length) to the indicated stretch ratios followed by a continuous orientation or stretching in the cross machine (width) direction to the indicated stretch ratios, followed by annealing. Microporous film characterization data are also reported in Table I.

The fluorochemical oxazolidinone (FCO) used to prepare the microporous films was similar to that described in U.S. Pat. No. 5,025,052 (Crater et al.) Example 1, except that the alcohol and isocyanate reactants used to prepare the oxazolidinone were $C_8F_{17}SO_2N(CH_3)CH_2CH(CH_2Cl)OH$ and $OCNC_{18}H_{37}$, respectively.

TABLE I

Microporous Film Compositions and Characterization

| Film MPF | Film Composition | Orientation Length | Width | Gurley Number (sec/50 cc) |
|---|---|---|---|---|
| 1 | PP[1]/FCO[2]/Blue[3]/MO[4] 64.6/1.5/0.9/33.0 | 1.8 | 1.6 | 326 |
| 2 | PP[1]/FCO[2]/Blue[3]/MO[4] 63/1.5/2.5/35.5 | 1.7 | 1.8 | 80 |
| 3 | PP[1]/FCO[2]/Blue[3]/MO[4] 63.0/1.5/2.5/35.5 | 1.8 | 1.8 | 51 |

TABLE I-continued

Microporous Film Compositions and Characterization

| Film MPF | Film Composition | Orientation Length | Width | Gurley Number (sec/50 cc) |
|---|---|---|---|---|
| 4 | PP[1]/FCO[2]/Blue[3]/MO[4] 61.3/1.5/2.5/34.7 | 1.6 | 1.8 | 39 |
| 5 | PP[1]/FCO[2]/Blue[3]/MO[4] 63.0/1.5/1.0/35.5 | 1.6 | 1.7 | 29 |
| C1 | PP[1]/Blue[3]/MO[4] 63.7/1.0/39.0 | 1.4 | 1.2 | 24 |

[1] 0.8 dg/min melt flow index polypropylene, available from Himont Inc., Wilmington DE under the trade designation PRO-FAX.
[2] Fluorochemical oxazolidinone as described above.
[3] Blue PP pigment BLUE P293C, available from PMS Consolidated, Somerset, NJ.
[4] Mineral Oil available from AMOCO Oil Company under the trade designation AMOCO White Mineral Oil #31 USP (Grade).

Particle Loaded BMF Preparation

Particle loaded blown microfiber (BMF) filter webs were prepared using a process similar to that described in, for example, Wente, Van A., "Superfine Thermoplastic Fibers" in *Industrial Chemistry*, Vol. 48, P.1342 et seq (1956), or in Report No. 4364 of the Naval Research Laboratories, published May 25, 1954 entitled "Manufacture of Superfine Organic Fibers," by Wente, V. A., Boone, C. D. and Fluharty, E. L. The BMF apparatus utilized, as noted, either an NLR die, as described in the above cited references, or a drilled die having circular smooth surface orifices (10/cm) having a 0.43 mm (0.017 inch) diameter and a 8:1 length to diameter ratio. Process variables for the BMF carrier webs and web characterization data are presented in Table II. An air pressure of 0.34–2.10 Bar (5–30 psi) with an air gap of 0.076 cm width was maintained for both the NLR and drilled dies and the polymer throughput rate was approximately 145 g/hr/cm die width for the polypropylene resins and approximately 179 g/hr/cm die width for the ethylene vinyl acetate resin blends.

TABLE II

BMF Carrier Web Process Variables

| Web BMF | Resin | Extrusion Temp. (°C.) | Primary Air Temp. (°C.) | Web Basis Wt. (gm/m²) | Avg. Fiber Diameter (microns) |
|---|---|---|---|---|---|
| 1 | PP[1] | 170–350 | 380 | 30 | 8.5 |
| 2 | PP[2] | 165–300 | 230 | 50 | 8.0 |
| 3 | EVA Blend[3] | 90–220 | 240 | 50 | 14.0 |
| 4 | PB Blend[4] | 170–350 | 270 | 100 | 8.9 |

[1] 3505 polypropylene resin (available from EXXON Chemical Co., Houston, TX).
[2] 3495G polypropylene resin (available from EXXON Chemical Co.).
[3] A 50/50 wt. % blend of EXXON VL 7520 ethylene vinyl acetate resin (available from EXXON Chemical Co.) and Quantum EY 902-35 ethylene vinyl acetate resin (available from Quantum Chemical Corp., Cincinnati, OH).
[4] A 75/25 wt. % blend of Shell polybutylene PB8910 (available from Shell Oil, Oak Brook, IL) and 3495G polypropylene resin.

Delivery of the adsorbent particles into the BMF carrier webs was accomplished by introducing the particles into a laminar air stream diffuser with a 1.9 cm (0.75 inch) eductor device and allowing the laminar air stream to distribute the particles before conveying them to the particle loader exit, causing the particles to mix with the microfiber stream, becoming either entangled in or bonded to fibers in the molten fiber stream before they reached the collector surface and solidified. The laminar air stream was produced by a 5 hp air blower supplying an air stream through an aerodynamically designed diffuser with a cone angle of 10 degrees. Air volume flow rate through the diffuser was variable and operated at less than 60 cubic feet per minute (SCFM). The eductor fed the particles to the converging air stream at a rate of 400 gm/minute or less with the eductor air volume flow of no more than 15 SCFM. The air volume flow and eductor particle feed were varied to produce the desired particle loading levels. Particulate adsorbent loaded BMF webs useful in the present invention are described in Table III.

TABLE III

Particulate Loaded BMF Filter Webs

| Adsorbent Web (ABW) | Carrier Web BMF | Adsorbent | Adsorbent Loading (wt. %) | Tested Service Life (minutes) |
|---|---|---|---|---|
| 1 | 4 | Activated Carbon[1] | 61 | <2.0 |
| 2 | 3 | Activated Carbon[2] | 82 | 15.6 |
| 3 | 2 | Activated Carbon[2] | 89 | >18 |
| 4 | 1 | Molecular Sieve[3] | 82 | <5.0 |

[1] Coconut carbon 80 × 200 mesh size, (available from Calgon Carbon Corp., Pittsburgh, PA).
[2] KINA 209C carbon, 80 × 200 mesh size (available from Barnebey and Sutcliffe Corp., Columbus, OH).
[3] ABSCENT ™ molecular sieves, (available from UOP Molecular Sieves, Tarrytown, NY).

The Calgon Carbon coconut carbon of filter web 1 was treated with a potassium carbonate solution. The KINA carbon of webs 2 and 3 was treated with a NaOH solution and a KI solution.

PARTICLE CONTAINMENT WEBS

A variety of nonwoven webs, including blown microfiber webs, carded webs, and spun bond webs can be used as particle containment webs for the filters of the present invention. Suitable webs have a permeability no less than that of the microporous film, but preferably more than that of the particle loaded BMF web, and will contain any adsorbent particulate material that dislodges from the particle loaded BMF webs. Additionally, the particle containment webs should be based on materials which will be readily bonded/sealable to the other components webs of the filter construction as well as to the film materials typically used in the manufacture of ostomy bags (i.e., ethylene vinylacetate/polyvinylidene chloride/ethylene vinylacetate laminate films). A representative sampling of particulate containment webs useful in fabricating filters of the present invention is provided in Table IV.

TABLE IV

Particle Containment Webs

| Particle Containment Web PCW | Description |
|---|---|
| 1 | BMF carrier web BMF-1, 30 gm/m² web based on an EVA resin blend (see description above) |
| 2 | 50 gm/m² carded web of 3.0 cm (1.2 inch) 2.2 denier polypropylene staple fiber, available from Hercules, Inc. Covington, GA, which was calendared at 171° C. and 800 psi |
| 3 | 50 gm/m² polypropylene spun bond web, available from Polybond, Inc., Charlottesville, VA |
| 4 | 17 gm/m² polypropylene spun bond web (centrifically spun), available from |

TABLE IV-continued

| Particle Containment Web PCW | Description |
|---|---|
| | AMOCO Fabrics and Fibers, Atlanta, GA |

FILTER ASSEMBLY

Procedure A

A unified sandwich construction of a microporous film (MPF), an adsorbent particle loaded BMF web (ABW), and a particle containment web (PCW) was prepared by cold welding a concentric stack of 45 mm diameter discs of the respective materials using a three pronged die consisting of a 24 mm diameter metal cylinder with a 1 mm thick wall machined to have three equally spaced arcs 3 mm in length. The webs were cold welded together by applying a hammer blow to the die as it was placed on a stack of the disks.

Procedure B

A unified sandwich construction of a microporous film, a particle loaded BMF web, and a particle containment web was prepared by ultrasonically sealing the perimeter of a concentric stack of a 45 mm diameter disc of microporous film, a 43 mm diameter disc of a particle loaded BMF web, and a 45 mm diameter disc of a particle containment webs using a Branson series 800 sealer (available from Branson Sonic Power Co., Danbury, Conn.) configured with a 51 mm (2 inch) diameter cylindrical aluminum horn, using a 0.5-1.0 second seal time, and a 0.5-1.0 second dwell time at 60 psi.

Procedure C

A unified sandwich construction of a microporous film, a particle loaded BMF web, and a particle containment web was prepared by heat sealing the perimeter of a concentric stack of a 45 mm diameter disc of microporous film, a 42 mm diameter disc of a particle loaded BMF web, and a 45 mm diameter disc of a particle containment web. The seal was achieved using a Contech press (available from Converting Tech. Inc., West Goodard, Kans.) with the upper platen maintained at 110° C., the lower platen maintained at 68° C. and using a 1.0 second dwell time at 500 psi with a 45 mm OD annular die having 3 mm thick walls.

Procedure D

A unified sandwich construction of a microporous film, a particle loaded BMF web, and a particle containment web was prepared by point bonding a layered assembly consisting of a microporous film, a particle loaded BMF web, and a particle containment web by passing the layered assembly through a point bond calendar having a regularly spaced pin pattern of 1.5 mm rectangular diameter pins which embossed approximately 15% of the web area, with the calendar operating at 200 psi, 93° C. (200° F.) and 3.7 m/min. (12 ft/min). 40 mm diameter discs were cut from the pin bonded laminate.

Independent of the procedure used to prepare the filter construction, the unified filter construction was then sealed to the outer face of the film material forming the ostomy bag with the microporous film layer of the filter assembly facing the interior of the ostomy bag. Sealing was typically accomplished by using a 40 mm OD annular die having 4 mm thick walls in a press maintained at 150° C. and using 50 psi pressure with a 0.5 second dwell time.

Constructions of various filters of the present invention are detailed in Table V along with the Gurley number, test service life and estimated service life, as determined by the previously described test procedures. Table V also includes Gurley number and service life data for filter constructions removed from commercially available ostomy bags.

TABLE V

Filter Construction and Performance

| Filter | MPF | ABW | PCW | Assembly | Gurley Number (sec/50 cc) | Tested Service Life (minutes) | Estimated Service Life (days) |
|---|---|---|---|---|---|---|---|
| 1 | 1 | 1 | 4 | D | 326 | <2.0[1] | 0.21 |
| 2 | 3 | 4 | 3 | A | 51 | <5.0 | 1.0 |
| 3 | 3 | 3 | 2 | B | 51 | >17 | >3.5 |
| 4 | 3 | 2 | 1 | A | 51 | 15.6 | 3.25 |
| 5 | 3 | 2 | 3 | A | 51 | 15.6 | 3.25 |
| 6 | 5 | 3 | 2 | B | 29 | 94 | 19.6 |
| 7 | 5 | 3 | 2 | C | 29 | >18 | >3.75 |
| 8 | 2 | 1 | 4 | D | 80 | <2.0 | 0.21 |
| 9 | C1 | 1 | 4 | D | 24 | <2.0 | 0.21 |
| Comp. 1[2] | — | — | — | — | — | <1.0 | 0.21 |
| Comp. 2[2] | — | — | — | — | — | 5 | 1.0 |
| Comp. 3[2] | — | — | — | — | — | <1.0 | 0.21 |

[1] Tested at a flow rate of 250 ml/min instead of the specified 500 ml/min.
[2] Filters removed from commercially available ostomy bags and tested under the same conditions as the filters of the present invention.

Filter constructions 1, 2, 8 and 9 while similar to the filter constructions of the present invention, provide filtration performance comparable to that displayed by filters (Comp. 1–Comp. 3) used on commercially available ostomy bags. Generally these constructions (1, 2, 8, and 9 and Comp. 1–Comp. 3) have significantly lower service lives (<5 minutes as tested, estimated as 1 day in actual use) than the filters of the present invention. The filters of the present invention minimally provide a factor 3X service life in terms of their adsorptive capacity as well as providing a fluorochemical containing microporous barrier layer which will minimize fouling of the filter construction by liquid and solid excrements.

We claim:

1. A filter for an ostomy appliance comprising at least one outer heat sealable liquid impermeable, gas permeable microporous film layer having a Gurley number of less than about 100 seconds/50 cc, an inner filter layer of adsorbent particles uniformly dispersed in a melt-blown microfiber web having a particle loading level such that a 40 mm diameter filter would provide an estimated service life of greater than 3 days on a typical ostomy appliance and a second outer porous cover layer, wherein the at least one outer heat sealable microporous film layer is on a first face of the inner filter layer and the porous cover layer is on a second face of the filter layer and the three layers are coextensive and continuous at least over the filter layer.

2. The ostomy filter of claim 1 wherein the filter layer is a melt-blown web having a basis weight of less than 700 gram/m$^2$.

3. The ostomy filter of claim 1 wherein the filter layer is a melt-blown web having a basis weight of less than 500 gram/m$^2$.

4. The ostomy filter of claim 3 wherein the filter layer is a melt-blown web having at least 80 percent by weight adsorbent granules.

5. The ostomy filter of claim 4 wherein the filter layer is a melt-blown web having at least 85 percent by weight adsorbent granules.

6. The ostomy filter of claim 1 wherein the adsorbent granules comprise acid gas adsorbent activated carbon granules.

7. The ostomy filter of claim 1 wherein the heat sealable microporous film layer is formed from a thermoplastic polymer with a soil resistant melt additive.

8. The ostomy filter of claim 7 wherein the soil resistant melt additive comprises a fluorochemical oxizolidinone.

9. The ostomy filter of claim 1 wherein the porous cover layer is a woven or non-woven web having a porosity greater than that of the microporous film layer and the microporous film layer has a Gurley value of less than 55 seconds/50 cc.

10. The ostomy filter of claim 1 wherein the porous cover layer, the filter layer and the microporous film layer are heat sealed to the adjacent filter layer and the filter layer has a thickness of less than 5 mm and is formed only of melt blown microfibers.

11. An ostomy appliance comprising heat sealable side walls at least one side wall having an opening, the outside face of said side wall having an opening having a heat sealable ostomy filter heat sealed around said opening by a heat sealable microporous film layer said filter comprising at least one outer heat sealable, liquid impermeable and gas permeable microporous film layer having a Gurley number of less than about 100 seconds/50 cc, an inner filter layer of adsorbent particles uniformly dispersed in a melt-blown microfiber web having a particle loading level such that a 40 mm diameter filter would provide an estimated service life of greater than 3 days on a typical ostomy appliance and a second outer porous cover layer, wherein at least one outer heat sealable microporous film layer is on a first face of the inner filter layer and the porous cover layer is on a second face of the filter layer and the three layers are coextensive and continuous over the filter layer, the coextensive and continuous filter layers extending into a peripheral region around the full circumference of the filter which peripheral region is heat sealed to the ostomy.

12. The ostomy appliance of claim 11 wherein the filter layer is a melt-blown web having a basis weight of less than 700 gram/m$^2$ and the microporous film Gurley value is less than 55 seconds/50 cc.

13. The ostomy appliance of claim 11 wherein the filter layer is a melt-blown web having a basis weight of less than 500 gram/m$^2$ and the microporous film Gurley value is less than 42 seconds/50 cc.

14. The ostomy appliance of claim 13 wherein the filter layer is a melt-blown web having at least 80 percent by weight adsorbent granules.

15. The ostomy appliance of claim 14 wherein the filter layer is a melt-blown web having at least 85 percent by weight adsorbent granules.

16. The ostomy appliance of claim 11 wherein the adsorbent granules comprise acid gas adsorbent activated carbon granules.

17. The ostomy appliance of claim 11 wherein the heat sealable microporous film is formed from a thermoplastic polymer with a soil resistant melt additive.

18. The ostomy appliance of claim 17 wherein the soil resistant melt additive comprises a fluorochemical oxizolidinone.

19. The ostomy appliance of claim 11 wherein the porous cover layer is a woven or non-woven web having a porosity greater than that of the microporous film layer.

20. The ostomy appliance of claim 11 wherein the porous cover layer, the filter layer and the microporous film layer are heat sealed to the adjacent filter layer and the filter layer has a thickness of less than and is formed only of melt blown microfibers.

* * * * *